United States Patent [19]
Harrison

[11] Patent Number: 5,929,016
[45] Date of Patent: Jul. 27, 1999

[54] LOW RESIDUE AQUEOUS HARD SURFACE CLEANING AND DISINFECTING COMPOSITIONS

[75] Inventor: Kenneth A. Harrison, Goshen, N.Y.

[73] Assignee: Reckitt & Colman Inc., Wayne, N.J.

[21] Appl. No.: 08/950,985

[22] Filed: Oct. 15, 1997

[30] Foreign Application Priority Data

Oct. 24, 1996 [GB] United Kingdom ............ 9622176

[51] Int. Cl.⁶ .................. C11D 1/75; C11D 1/62; C11D 3/43
[52] U.S. Cl. ................ 510/384; 510/199; 510/235; 510/237; 510/362; 510/363; 510/382; 510/409; 510/411; 510/424; 510/490; 510/503; 510/504
[58] Field of Search ................ 510/199, 235, 510/237, 362, 363, 382, 384, 409, 411, 424, 490, 503, 504

[56] References Cited

U.S. PATENT DOCUMENTS

| | | | |
|---|---|---|---|
| 3,882,038 | 5/1975 | Clayton et al. | 252/89 |
| 4,576,729 | 3/1986 | Paszek et al. | 252/106 |
| 4,820,450 | 4/1989 | Wile et al. | 252/545 |
| 5,403,587 | 4/1995 | McCue et al. | 424/195.1 |
| 5,435,935 | 7/1995 | Kupneski | 252/156 |
| 5,454,983 | 10/1995 | Michael et al. | 252/545 |
| 5,522,942 | 6/1996 | Graubart et al. | 134/40 |
| 5,750,482 | 5/1998 | Cummings | 510/182 |

FOREIGN PATENT DOCUMENTS

| | | | |
|---|---|---|---|
| 0 129 980 A2 | 1/1985 | European Pat. Off. | C11D 3/48 |
| 0 621 335 A2 | 10/1994 | European Pat. Off. | C11D 1/835 |
| 0 691 397 A2 | 1/1996 | European Pat. Off. | C11D 3/00 |
| 0691397 | 10/1996 | European Pat. Off. | |
| 2 247 243 | 2/1992 | United Kingdom | C11D 3/43 |
| WO94/22996 | 10/1994 | WIPO | C11D 1/75 |
| WO95/14757 | 6/1995 | WIPO | C11D 3/20 |

OTHER PUBLICATIONS

Copy of GB Search Report dated Jan. 17, 1997 for GB Application No. 9622176.7.
Copy of PCT Search Report dated Feb. 11, 1998 for PCT Application No. PCT/US97/18774.

*Primary Examiner*—Yogendra N. Gupta
*Assistant Examiner*—Charles Boyer
*Attorney, Agent, or Firm*—Fish & Richardson P.C.

[57] ABSTRACT

Aqueous based cleaning compositions simultaneously featuring disinfecting, low residue deposit and good cleaning characteristics are provided. The compositions include one or more quaternary amine compounds as disinfecting active agents, an organic solvent system which includes glycol mono-n-butyl ether or a binary system including a glycol ether with a linear primary alcohol, and either one or more betaines, or one or more amine oxides as a surfactant constituent.

17 Claims, No Drawings

LOW RESIDUE AQUEOUS HARD SURFACE CLEANING AND DISINFECTING COMPOSITIONS

Cleaning compositions are commercially important products and enjoy a wide field of utility in assisting in the removal of dirt and grime from surfaces, especially those characterized as useful with "hard surfaces". Hard surfaces are those which are frequently encountered in lavatories such as lavatory fixtures such as toilets, shower stalls, bathtubs, bidets, sinks, etc., as well as countertops, walls, floors, etc.

While the art is replete with various formulations which provide some cleaning benefit and perhaps some disinfecting benefit to surfaces, few such formulations are sufficiently formulated so to be effective sanitizing and cleaning compositions and to appropriately satisfy the registration requirements of the United States Environmental Protection Administration as a "hospital strength" disinfectant.

Thus, it is understood that there is a present and continuing need for cleaning products which simultaneously disinfect, leave a minimum of discernible residue, clean well, and are inexpensive. This need is further heightened when considered conjointly with the need for compositions which meet current requirements of the United States' Environmental Protection Administration, especially as hospital strength disinfecting compositions.

The invention is a aqueous liquid disinfectant cleaner which is particularly useful for cleaning and disinfecting hard surfaces.

Thus, it is among the objects of the invention to provide improved aqueous cleaning compositions which are especially useful in cleaning and disinfecting, especially hard surfaces.

It is a still further object of the invention to provide improved aqueous ready to use cleaning compositions which exhibit a low tendency to leave surface residues upon treated surfaces, especially hard surfaces.

It is a further object of the invention to provide a shelf stable aqueous cleaning and disinfecting composition which does not undesirably degrade when subjected to an elevated temperature over an extended period of time.

It is yet a further object of the invention to provide a readily pourable and readily pumpable aqueous cleaning composition which features the benefits described above.

It is still further object of the invention to provide an aqueous cleaning and disinfecting composition which may be categorized as a hospital strength disinfecting composition in accordance with current United States Environmental Protection Administration requirements.

It is a further object of the invention to provide a process for the simultaneous cleaning and sanitization of hard surfaces, which process comprises the step of: providing an aqueous cleaning composition as outlined above, and applying an effective amount of the same to a surface, especially a hard surface requiring such cleaning and sanitizing treatment.

These and other objects of the invention shall be more apparent from a reading of the specification and of the claims attached.

According to one aspect of the present invention there is provided an aqueous cleaning composition which provides disinfecting and cleaning characteristics to treated surfaces, particularly hard surfaces, which comprises the following constituents:

A) a quaternary ammonium surfactant compound having germicidal properties;

B) a solvent system selected from: propylene glycol n-butyl ether, or, a binary solvent combination of a glycol ether with a linear primary alcohol, especially linear primary $C_6$–$C_{18}$ alcohols;

C) a surfactant compound selected from betaine or amine oxide compounds;

D) an alkanolamine;

E) water.

The compositions may include one or more further optional additive constituents, sometimes referred to as adjuvants, in minor, but effective amounts. By way of non-limiting example, such optional additives include: coloring agents such as dyes and pigments, fragrances, other pH adjusting agents, pH buffer compositions, chelating agents, rheology modification agents as well as one or more further surfactant compounds, in particular nonionic surfactant compounds. Desirably, in order to reduce the likelihood of undesired buildup upon treated surfaces, especially hard surfaces, the amounts of these additive constituents are present in only minor amounts, i.e., less than 5% wt. based on the total weight of the aqueous cleaning composition being provided herein. The compositions are characterized in providing a disinfecting effect, desirably sufficient to be rated a "broad spectrum disinfectant" yet more desirably sufficient to be rated a "hospital strength disinfectant".

A) The compositions according to the invention include one or more quaternary ammonium surfactant compounds having germicidal properties. Exemplary useful quaternary ammonium compounds and salts thereof include quaternary ammonium germicides which may be characterized by the general structural formula:

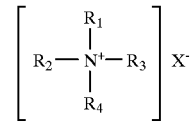

where at least one of $R_1$, $R_2$, $R_3$ and $R_4$ is a alkyl, aryl or alkylaryl substituent of from 6 to 26 carbon atoms, and desirably the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxyalkyl, arylalkyl, etc. The remaining substituents on the nitrogen atoms other than the abovementioned alkyl substituents are hydrocarbons usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits water solubility of the quaternary ammonium complex. Exemplary counterions include halides, for example chloride, bromide or iodide, or methosulfate.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide, ether or ester linkages such as octyl phenoxy ethoxy ethyl dimethyl benzyl ammonium chloride, N-(laurylcocoaminoformylmethyl)pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which act as germicides and which are be found useful in the practice of the present invention include those which have the structural formula:

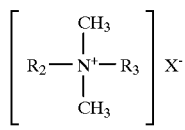

wherein $R_2$, and $R_3$ are the same or different $C_8$–$C_{12}$alkyl, or $R_2$ is $C_{12-16}$alkyl, $C_{8-18}$alkylethoxy, $C_{8-18}$alkylphenolethoxy and $R_3$ is benzyl, and X is a halide, for example chloride, bromide or iodide, or methosulfate. The alkyl groups recited in $R_2$ and $R_3$ may be straight-chained or branched, but are preferably substantially linear.

Particularly useful quaternary germicides include compositions which include a single quaternary compound, as well as mixtures of two or more different quaternary compounds. Particularly useful quaternary germicides include which are described as being a blend of alkyl dimethyl benzyl ammonium chlorides; BARDAC® 205M, BARDAC® 2050, BARDAC® 2080, BARDAC® 2250, BTC® 812, BTC® 818 and BTC® 1010 which are described as being based on dialkyl($C_8$–$C_{10}$)dimethyl ammonium chloride; BARDAC® 2250 and BARDAC® 2280 or BTC® 1010 which are described as being a composition which includes didecyl dimethyl ammonium chloride; BARDAC® LF and BARDAC® LF 80 which are described as being based on dioctyl dimethyl ammonium chloride; BARQUAT® MB-50, BARQUAT® MB-80, BARQUAT® MX-50, BARQUAT® MX-80, BARQUAT® OJ-50, BARQUAT® OJ-80, BARDAC® 208M, HYAMINE® 3500, HYAMINE® 3500-NF, BTC® 50, BTC® 824, BTC® 835, BTC® 885, BTC® 2565, BTC® 2658, BTC® 8248 or BTC® 8358 each described as being based on alkyl dimethyl benzyl ammonium chloride (benzalkonium chloride); BARQUAT® 4250, BARQUAT® 4280, BARQUAT® 4250Z, BARQUAT® 4280Z, BTC® 471, BTC® 2125, or BTC® 2125M each described as being a composition based on alkyldimethylbenzyl ammonium chloride and/or alkyldimethylethylbenzyl ammonium chloride; BARQUAT® MS-100 or BTC® 324-P-100 each described as being based on myristyldimethylbenzyl ammonium chloride; HYAMINE® 2389 described as being based on methyldodecylbenzyl ammonium chloride and/or methyldodecylxylene-bis-trimethyl ammonium chloride; HYAMINE® 1622 described as being an aqueous solution of benzethonium chloride; as well as BARQUAT® 1552 or BTC® 776 described as being based on alkyl dimethyl benzyl ammonium chloride and/or dialkyl methyl benzyl ammonium chloride, BARQUAT® 50-MAB described as being based on alkyldimethylethyl ammonium bromide and LONZABAC®-12.100 described as being based on an alkyl tertiary amine. Polymeric quaternary ammonium salts based on these monomeric structures are also considered desirable for the present invention. One example is POLYQUAT® described as being a 2-butenyldimethyl ammonium chloride polymer. (Each of these recited materials are presently commercially available from Lonza, Inc., Fairlawn, N.J. and/or from Stepan Co., Northfield Ill.)

In the cleaning compositions according to the invention, the quaternary ammonium compound constituent is required to be present in amounts which are effective in exhibiting satisfactory germicidal activity against selected bacteria sought to be treated by the cleaning compositions. Such efficacy may be achieved against less resistant bacterial strains with only minor amounts of the quaternary ammonium compounds being present, while more resistant strains of bacteria require greater amounts of the quartenary ammonium compounds in order to destroy these more resistant strains. The quaternary ammonium compound need only pre present in germicidally effective amounts. Generally, effective "hospital strength" germicidal efficacy meeting current EPA guidelines is provided when the quaternary ammonium compounds are present in an amount of from about 0.05% wt. to about 3% wt. Desirably the quaternary ammonium compounds is present in an amount of from 0.08% wt. to about 0.5% wt, and yet more desirably from 0.08% wt. to 0.15% wt. based on the total weight of the inventive compositions being taught herein.

B) The compositions of the invention include an organic solvent system selected from propylene glycol n-butyl ether, or, a binary solvent combination of a glycol ether with a linear primary alcohol.

Surprisingly, the inventor has found that unlike other glycol ethers, propylene glycol n-butyl ether has been observed to quickly evaporate in a relatively even manner such that it tends to form a relatively uniform film layer during the drying process. Such is an advantageous feature of the instant invention as it is to be understood that the rate at which the volatile components appear to evaporate from the treated surface, and the physical form (pattern) assumed by the nonvolatile materials deposited on the surface after the volatile components have evaporated are directly related to the perception by the consumer of the cleaning efficacy and of surface residue left by a composition. Thus, the propylene glycol n-butyl ether solvent is selected as being not only effective in solubilizing deposited soils, especially from hard surfaces, but also those which simultaneously are observed to evaporate rapidly and which form a relatively uniform film on the treated surface during the drying process as opposed to those which impart a mottled or streaky appearance to the treated surface during drying, as with other glycol ethers. Such undesirable characteristics are believed to be attributable to a pooling effect, where the volatile constituents of the compositions are observed to draw the nonvolatile constituents into visible and nonuniform patterns of deposition as the volatile constituents evaporate. These patterned deposits are often very conspicuous, and are visible as surface mottling or streaking of the composition as it evaporates, as well as subsequent to evaporation as any nonvolatile materials in the compositions are deposited in an uneven manner. Such undesirable drying characteristics are overcome by the compositions of the invention, particularly in preferred embodiments thereof.

The present inventor has found that attempts to substitute the propylene glycol n-butyl ether with a different glycol ether solvent is generally unsuccessful as such different glycol ethers, even of very similar molecular structures, and their compositions have been observed not to form a relatively uniform film on the treated surface during the drying process, and have been observed to cause an uneven or mottled appearance as the compositions evaporate. This is a surprising result as generally, similar glycol ethers have been known to be substitutable in many compositions. This is not so in the present compositions. However, the present inventor has observed that such a detriment attendant upon the use of different glycol ether solvents may be overcome by the addition to such glycol ether solvents, other than propylene glycol n-butyl ether of an effective amount of a linear primary alcohol, preferably a linear primary $C_6$–$C_{18}$ alcohols, with those of higher chain lengths $C_8$–$C_{18}$ as being preferred. The inclusion of such linear primary alcohols have been found by the present inventor to beneficially assist in the evaporation of a composition in a relatively even manner such that it tends to form a relatively uniform film layer during the drying process. This effect has been generally described above in conjunction with glycol n-butyl ethers. A further benefit of the inclusion of such linear primary alcohols is in the solvency which they may provide to certain stains as well. It is also contemplated that such a linear primary alcohol may be used in conjunction with propylene glycol n-butyl ether solvent, although the alcohol is not necessary.

Exemplary useful glycol ethers include the glycol ethers having the general structure $R_a$—O—$R_b$—OH, wherein $R_a$ is an alkoxy of 1 to 20 carbon atoms, or aryloxy of at least 6 carbon atoms, and $R_b$ is an ether condensate of propylene glycol and/or ethylene glycol having from one to ten glycol monomer units. Preferred are glycol ethers having one to five glycol monomer units. These are $C_3$–$C_{20}$ glycol ethers. Examples of more preferred glycol ethers include those denoted in the Examples below, which include propylene glycol n-butyl ether and dipropylene glycol n-butyl ether. Such materials are commercially available in the DOW-ANOL® series from The Dow Chemical Company, Midland Mich., as well as in the ARCOSOLV® P series from Arco Chemical Co., Newton Square Pa. It is to be noted that such preferred glycol ethers are ones which feature limited solubility in water, generally about 20 ml or less per 100 ml water at room temperature.

Where the organic solvent system (B) consists solely of a propylene glycol n-butyl ether solvent, it is desirably present in amounts of up to about 6% wt., more desirably is present in an amount of from about 0.001% wt to about 5% wt, and most desirably is present in an amount of from 1.0% wt.–4.5% wt. based on the total weight of the aqueous composition.

Where the organic solvent system (B) consists of a glycol ether solvent other than propylene glycol n-butyl ether in conjunction with a primary linear alcohol, these constituents are together desirably present in amounts of up to about 6% wt., more desirably is present in an amount of from about 0.001% wt to about 5% wt, and most desirably is present in an amount of from 3% wt.–4.5% wt. based on the total weight of the aqueous composition. In such a composition the amount of the linear primary alcohol present is only a small fraction of the total amount of the organic solvent system (B), and generally forms about 25% wt. and less of the total amount of the organic solvent system (B). It has also been observed that as the chain length of the linear primary alcohol is increased from $C_6$, a lesser amount of the linear primary alcohol need be present while maintaining the desirable drying characteristics described above.

C) The present inventive compositions include one or more surfactant compounds selected from betaine compounds and amine oxide compounds. Such nonionic surfactants are known to the art and are available in commercial preparations, typically as a quantity of the surfactant compound dispersed in an aqueous carrier.

Such betaine compounds or amine oxide compounds are particularly selected from other known surfactant compounds as they have been observed to provide not only requisite surface active characteristics and, compatibility with the quaternary ammonium cationic compounds but also have been observed by the inventor to assist in maintaining the phase stability of the inventive compositions over extended intervals of time and/or at high temperatures, up to about 120° F. Generally the compositions do not undergo phase separation at these temperatures. Such beneficial characteristics have been observed especially where the organic solvent is selected to be among the preferred, in particular to be the most preferred organic solvent. Further, the present inventor has observed that these betaine compounds or amine oxide compounds do not tend to contribute to a mottled or streaky appearance to the treated surface during drying, as has been described in more detail above. Additionally, these betaine compounds or amine oxide compounds provide a cleaning benefit to the compositions.

Betaine compounds which are useful in the compositions of the invention are known to the art. By way of non-limiting example, exemplary betaines include compounds according to the general formula:

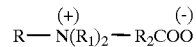

wherein R is a hydrophobic group selected from the group consisting of alkyl groups containing from about 10 to about 22 carbon atoms, preferably from about 12 to about 18 carbon atoms, alkyl aryl and aryl alkyl groups containing a similar number of carbon atoms with a benzene ring being treated as equivalent to about 2 carbon atoms, and similar structures interrupted by amido or ether linkages; each $R_1$ is an alkyl group containing from 1 to about 3 carbon atoms; and $R_2$ is an alkylene group containing from 1 to about 6 carbon atoms. Examples of preferred betaines include Mackam® DZ from the McIntyre Group Ltd. Sulfobetaines may also be used in the inventive compositions. These include Rewoteric® AM HC and Rewoteric® AM CAS Uf from Witco Corp. These betaine compounds, when present, comprise 0.1–4.0% wt. of the inventive compositions, but more preferably comprise 2.0–4.0% wt.

Amine oxide compounds which are useful in the compositions of the invention are known to the art. One general class of useful amine oxides include alkyl di(lower alkyl) amine oxides in which the alkyl group has about 10–20, and preferably 12–16 carbon atoms, and can be straight or branched chain, saturated or unsaturated. The lower alkyl groups include between 1 and 7 carbon atoms. Examples include lauryl dimethyl amine oxide, myristyl dimethyl amine oxide, dimethyl cocoamine oxide, dimethyl (hydrogenated tallow)amine oxide, and myristyl/palmityl dimethyl amine oxide.

A further class of useful amine oxides includes alkyl di(hydroxy lower alkyl)amine oxides in which the alkyl group has about 10–20, and preferably 12–16 carbon atoms, and can be straight or branched chain, saturated or unsaturated. Examples are bis(2-hydroxyethyl)cocoamine oxide, bis(2-hydroxyethyl)tallow amine oxide, and bis(2-hydroxyethyl)stearylamine oxide.

Further useful amine oxides include those which may be characterized as alkylamidopropyl di(lower alkyl)amine oxides in which the alkyl group has about 10–20, and preferably 12–16 carbon atoms, and can be straight or branched chain, saturated or unsaturated. Examples are cocoamidopropyl dimethyl amine oxide and tallowamidopropyl dimethyl amine oxide.

Additional useful amine oxides include those which may be referred to as alkylmorpholine oxides in which the alkyl group has about 10–20, and preferably 12–16 carbon atoms, and can be straight or branched chain, saturated or unsaturated. Further examples of such include surfactant compositions based on amine oxides include those which are presently commercially available and include those under the trade name Ammonyx® (Stepan Co., Chicago Ill.), as well as Barlox® (Lonza Inc., Fairlawn N.J.) Amine oxides are generally preferred over the betaines, as it has been found by the inventor that the amine oxides, especially lauryl dimethyl amine oxide, provide substantially better cleaning than the betaine compounds which may also form part of the inventive compositions. With respect to the amine oxides, preferred are the alkyl di(lower alkyl)amine oxides in which the alkyl group has about 12–16 carbon atoms, of which most preferably lauryl amine oxides are used in the inventive compositions. Most preferably the amine oxide constituent is lauryl dimethyl amine oxide.

These amine oxide compounds, when present, comprise 0.1–4.0% wt. of the inventive compositions, but more preferably comprise 0.1–1.0% wt. of the inventive compositions.

D) The inventive compositions also include as the alkanolamines one or more alkanolamines, including mono-, di- and tri-alkanolamines. Preferred alkanolamines are lower alkanolamines have been found to provide alkalinity to the compositions and act as a pH adjusting agent. Exemplary lower alkanolamines include for example; ethanolamine, diethanolamine, triethanolamine and isopropanolamine. Desirably the alkanolamine component includes monoethanolamine, which has also been found to evaporate relatively quickly from treated surfaces in a uniform manner. Most desirably the alkanolamine constituent is only monoethanolamine. The alkanolamine constituent comprises from 0.001–3.0% wt. of the inventive compositions, but more preferably are present in amounts of from 0.1–0.5% wt.

As is noted above, the compositions according to the invention are aqueous in nature. Water is added in order to provide to 100% by weight of the compositions of the invention. The water may be tap water, but is preferably distilled and is most preferably deionized water. If the water is tap water, it is preferably substantially free of any undesirable impurities such as organics or inorganics, especially minerals salts which are present in hard water which may thus undesirably interfere with the operation of the constituents present in the aqueous compositions according to the invention, and/or contribute to the appearance of residues in the evaporating inventive compositions.

In particularly preferred embodiments, the inventive compositions are shelf stable aqueous cleaning and disinfecting composition which do not undesirably degrade when subjected to an elevated temperature over an extended period of time. More specifically, the inventive compositions do not suffer precipitation or phase separation when a sample composition is subjected to an accelerated ageing testing at 120 deg. F., for a four-week test period. As is known to the art, such a test is a harsh test, and a useful indicator of the long term shelf stability of the tested sample composition.

The compositions according to the invention may be categorized as "broad spectrum" disinfecting compositions as they exhibit antimicrobial efficacy against at least *Staphylococcus aureus,* and *Salmonella choleraesuis* in accordance with the AOAC Use-dilution Test known to those skilled in the art. In more preferred embodiments, the compositions according to the invention may be categorized as "hospital strength" type disinfecting compositions as they exhibit antimicrobial efficacy against all three of the bacteria: *Staphylococcus aureus, Salmonella choleraesuis,* and *Pseudomonas aeruginosa* in accordance with the AOAC Use-dilution Test method which evaluates the antimicrobial efficacy of a composition against *Staphylococcus aureus* (gram positive type pathogenic bacteria) (ATCC 6538), *Salmonella choleraesuis* (gram negative type pathogenic bacteria) (ATCC 10708), and *Pseudomonas aeruginosa* (ATCC 15442). The testing is performed generally in accordance with the protocols outlined in "Use-Dilution Method", Protocols 955.14, 955.15 and 964.02 described in Chapter 6 of "Official Methods of Analysis", 16th Edition, of the Association of Official Analytical Chemists; "Germicidal and Detergent Sanitizing Action of Disinfectants", 960.09 described in Chapter 6 of "Official Methods of Analysis", 15th Edition, of the Association of Official Analytical Chemists; or American Society for Testing and Materials (ASTM) E 1054-91 the contents of which are herein incorporated by reference. This test is also commonly referred to as the "AOAC Use-Dilution Test Method".

In preferred and especially in most preferred embodiments of the invention the compositions may be characterized in forming a substantially uniform film during drying from a hard surface. More particularly, when preferred compositions of the invention are applied to a hard surface and then formed into a film, such as will be performed by wiping the composition so to generally uniformly spread it onto the hard surface in a thin layer and then permitted to dry, the compositions dry without portions of the uniform film coalescing into droplets or rivulets. The uniform film of the compositions tend to dry in a uniform pattern, generally with noticeable drying beginning at the edges or margins of the uniform film, and proceeding to the central region of the uniform film. This description may of course vary, particularly where the film formed of the inventive compositions are wiped onto a hard surface but is not formed into a film of generally uniform thickness; in which case drying generally begins at the edges and proceeds to the thicker parts of the film which do not necessarily need to be in the center region. The overall drying effect, that of uniform drying without coalescing into droplets or rivulets however remains the same. Such a behavior is particularly advantageous in the cleaning and/or disinfecting treatment of a hard surface in need of said treatment. Subsequent to application, the composition then tends to dry in a generally uniform manner from a film as described above. This is particularly true where subsequent to an application on a hard surface, such as by spraying, the consumer spreads the deposited composition over a broader area of the hard surface such as by wiping with a rag, towel, paper towel or the like which form the composition into a thin film. The benefits of drying without coalescing into rivulets or droplets also ensures that substantial visually discernible deposits of non-evaporable constituents of the composition do not form. This is a problem with may compositions in the prior art, as during drying form a coalesced rivulet or droplet frequently any non-evaporable constituents deposit at the edges of the coalesced rivulet or droplet and are visible subsequent to drying as an outline of the now evaporated coalesced rivulet or droplet. This results in visibly discernible streaks or a mottled appearance when dried on a hard surface, especially on a highly reflective hard surface such as glazed tile or polished metal surfaces. This is unattractive to the consumer and usually requires a post application buffing or polishing step by the user of a product. This undesirable characteristic is generally avoided by the compositions of the invention, especially in preferred embodiments thereof.

As noted, the compositions may include one or more optional additives which by way of non-limiting example include: coloring agents such as dyes and pigments, fragrances and fragrance solubilizers, pH adjusting agents, pH buffering agents, chelating agents, rheology modification agents, as well as one or more further nonionic surfactant compounds. Desirably, in order to reduce the likelihood of undesired buildup upon treated surfaces, especially hard surfaces, the total amounts of such optional additives is less than about 2.5% wt. but are desirably significantly less, such as less than about 0.5% wt. based on the total weight of the aqueous cleaning and disinfecting composition being provided herein. Optimally, the amounts of such further optional additives is kept to a minimum in order to minimize the amounts of non-volatile constituents in the compositions as a whole, which tend to contribute to an undesired streaky or mottled appearance of the composition during drying.

Useful as chelating agents include those known to the art, including by way of non-limiting example; aminopolycarboxylic acids and salts thereof wherein the amino nitrogen has attached thereto two or more substituent groups. Preferred chelating agents include acids and salts, especially the sodium and potassium salts of ethylenediaminetetraacetic acid, diethylenetriaminepentaacetic acid, N-hydroxyethylethylenediaminetriacetic acid, and of which the sodium salts of ethylenediaminetetraacetic acid may be particularly advantageously used. Such chelating agents may be omitted, or they may be included in generally minor amounts such as from 0–0.5% wt. based on the weight of the chelating agents and/or salt forms thereof. Desirably, such chelating agents are included in the present inventive composition in amounts from 0–0.5% wt., but are most desirably present in reduced weight percentages from about 0–0.2% wt.

The compositions according to the invention optionally but desirably include an amount of a pH adjusting agent or pH buffer composition. Such compositions include many which are known to the art and which are conventionally used. By way of non-limiting example pH adjusting agents include phosphorus containing compounds, monovalent and polyvalent salts such as of silicates, carbonates, and borates, certain acids and bases, tartrates and certain acetates. Further exemplary pH adjusting agents include mineral acids, basic compositions, and organic acids, which are typically required in only minor amounts. By way of further non-limiting example pH buffering compositions include the alkali metal phosphates, polyphosphates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use as buffers such materials as aluminosilicates (zeolites), borates, aluminates and certain organic materials such as gluconates, succinates, maleates, and their alkali metal salts. Desirably the compositions according to the invention include an effective amount of an organic acid and/or an inorganic salt form thereof which may be used to adjust and maintain the pH of the compositions of the invention to the desired pH range. Particularly useful is citric acid and metal salts thereof such as sodium citrate which are widely available and which are effective in providing these pH adjustment and buffering effects. These should be screened however to ensure that they do not undesirably complex with or in other ways deactivate the quaternary ammonium compound(s).

Further optional, but advantageously included constituents are one or more coloring agents which find use in modifying the appearance of the compositions and enhance their appearance from the perspective of a consumer or other end user. Known coloring agents may be incorporated in the compositions in any effective amount to improve or impart to compositions a desired appearance or color. Such a coloring agent or coloring agents may be added in a conventional fashion, i.e., admixing to a composition or blending with other constituents used to form a composition.

Further optional, but desirable constituent include fragrances, natural or synthetically produced. Such fragrances may be added in any conventional manner, admixing to a composition or blending with other constituents used to form a composition, in amounts which are found to be useful to enhance or impart the desired scent characteristic to the composition, and/or to cleaning compositions formed therefrom.

In compositions which include a fragrance, it is frequently desirable to include a fragrance solubilizer which assists in the dispersion, solution or mixing of the fragrance constituent in an aqueous base. These include known art compounds, including condensates of 2 to 30 moles of ethylene oxide with sorbitan mono- and tri-$C_{10}$–$C_{20}$ alkanoic acid known to be useful as nonionic surfactants. Further examples of such suitable surfactants include water soluble nonionic surfactants of which many are commercially known and by way of non-limiting example include the primary aliphatic alcohol ethoxylates, secondary aliphatic alcohol ethoxylates, alkylphenol ethoxylates and ethylene-oxide-propylene oxide condensates on primary alkanols, and condensates of ethylene oxide with sorbitan fatty acid esters. This fragrance solubilizer component is added in minor amounts, particularly amount which are found effective in aiding in the solubilization of the fragrance component, but not in any significantly greater proportion, such that it would be considered as a detergent constituent. Such minor amounts of fragrance solubilizer recited herein is generally up to about 0.3% by weight of the fragrance constituent in the inventive compositions but is more generally an amount of about 0.1% by weight and less, and preferably is present in amounts of about 0.05% by weight and less.

As an optional constituent, the compositions may include one or more nonionic surfactant compounds in amounts which are effective in improving the overall cleaning efficacy of the compositions being taught herein, while at the same time in amounts which do not undesirably diminish the germicidal efficacy of the inventive compositions or which undesirably increase the likelihood to form or deposit surface residues onto the treated surfaces. Such nonionic surfactant compounds are known to the art.. Practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic surfactant compound. Further, the length of the polyethylenoxy hydrophobic and hydrophilic elements may be varied. Exemplary nonionic compounds include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides.

To be mentioned as particularly useful nonionic surfactants are alkoxylated linear primary and secondary alcohols such as those commercially available under the tradenames PolyTergent® SL series (Olin Chemical Co., Stamford Conn.), Neodol® series (Shell Chemical Co., Houston Tex.); as alkoxylated alkyl phenols including those commercially available under the tradename Triton® X series (Union Carbide Chem. Co., Danbury Conn.).

Such constituents as described above as essential and/or optional constituents include known art compositions, include those described in *McCutcheon's Emulsifiers and Detergents* (Vol. 1), *McCutcheon's Functional Materials* (Vol. 2), North American Edition, 1991; *Kirk-Othmer, Encyclopedia of Chemical Technology*, 3rd Ed., Vol. 22, pp. 346–387, the contents of which are herein incorporated by reference.

In accordance with a first preferred embodiment of the inventive composition, there is provided low residue ready to use aqueous hard surface cleaning and broad spectrum disinfecting, preferably hospital strength disinfecting compositions comprising per 100% wt., preferably consisting essentially of, per 100% wt:

0.05–0.3% wt. of a quaternary ammonium surfactant compound having germicidal properties;

0.5–10.0% wt., preferably from 1.0–4.5% wt. of propylene glycol mono-n-butyl ether;

0.1–4.0% wt. of one or more surfactant compounds selected from betaine or amine oxide compounds, but desirably is 0.1–3.0% wt. of one or more amine oxide compounds;

0.1–0.5% wt. one or more alkanolamines, desirably is only monoethanolamine;

0–0.5% wt. of one or more optional constituents;

to 100% water, wherein the compositions are characterized by forming a substantially uniform film during evaporative drying after being applied to a hard surface. In especially preferred embodiments, the compositions are also phase stable, and maintain phase stability when subjected to an elevated temperature of 120° F. for a period of at least 4 weeks.

In accordance with a second preferred embodiment of the inventive composition, there is provided a low residue ready to use aqueous hard surface cleaning and broad spectrum disinfecting, preferably hospital strength disinfecting compositions comprising per 100% wt., preferably consisting essentially of per 100% wt:

0.05–0.3% wt. of a quaternary ammonium surfactant compound having germicidal properties;

0.5–10.0% wt. of an organic solvent system which includes a glycol ether other than propylene glycol mono-n-butyl ether and a $C_6$–$C_{18}$ linear primary alcohol, and preferably is dipropylene glycol n-butyl ether and a $C_6$–$C_{18}$ linear primary alcohol;

0.1–4.0% wt. of one or more surfactant compounds selected from betaine or amine oxide compounds, but desirably is 0.1–3.0% wt. of one or more amine oxide compounds;

0.1–0.5% wt. one or more alkanolamines, desirably is only monoethanolamine;

0–0.5% wt. of one or more optional constituents;

to 100% water, wherein the compositions are characterized by forming a substantially uniform film during evaporative drying after being applied to a hard surface. In especially preferred embodiments, the compositions are also phase stable, and maintain phase stability when subjected to an elevated temperature of 120° F. for a period of at least 4 weeks.

The compositions of the invention can be prepared in a conventional manner such as by simply mixing the constituents in order to form the ultimate aqueous cleaning composition. The order of addition is not critical. Desirably, and from all practicable purposes, it is advantageous that the constituents other than water be added to a proportion of the total amount of water then well mixed, and most desirably that the surface active agents be first added to the volume of water, followed by any remaining ingredients such as the optional constituents. Subsequently any remaining balance of water, if any should be required, is then added.

The compositions according to the invention are useful in the cleaning and/or disinfecting of surfaces, especially hard surfaces, having deposited soil thereon. The compositions are particularly effective in the removal of oleophilic soils (viz., oily soils) particularly of the type which are typically encountered in kitchens and other food preparation environments. In such a process, cleaning and disinfecting of such surfaces comprises the step of applying a soil releasing and disinfecting effective amount of a composition as taught herein to such a soiled surface. Afterwards, the compositions are optionally but desirably wiped, scrubbed or otherwise physically contacted with the hard surface, and further optionally, may be subsequently rinsed from such a cleaned and disinfected hard surface.

The hard surface cleaner composition provided according to the invention can be desirably provided as a ready to use product in a manually operated spray dispensing container. Such a typical container is generally made of synthetic polymer plastic material such as polyethylene, polypropylene, polyvinyl chloride, polyethylene terephthalate, polybutylene terephthalate or the like and includes spray nozzle, a dip tube and associated pump dispensing parts and is thus ideally suited for use in a consumer "spray and wipe" application. In such an application, the consumer generally applies an effective amount of the cleaning composition using the pump and within a few moments thereafter, wipes off the treated area with a rag, towel, or sponge, usually a disposable paper towel or sponge. In certain applications, however, especially where undesirable soil deposits are heavy, the cleaning composition according to the invention may be left on the soiled area until it has effectively loosened the soil deposits after which it may then be wiped off, rinsed off, or otherwise removed. For particularly heavy deposits of such undesired soils, multiple applications may also be used. To ensure effective disinfection, a longer contact time, generally of 10 minutes or more is required. The uniform drying characteristics of the inventive compositions provide uniform drying even where the compositions are left for such a longer contact time.

In a yet a further embodiment, the compositions according to the invention may be formulated so that they may be useful in conjunction with an "aerosol" type product wherein they are discharged from a pressurized aerosol container. If the inventive compositions are used in an aerosol type product, it is preferred that corrosion resistant aerosol containers such as coated or lined aerosol containers be used. Such are preferred as they are known to be resistant to the effects of acidic formulations. Known art propellants such as liquid propellants as well as propellants of the non-liquid form, i.e., pressurized gases, including carbon dioxide, air, nitrogen, hydrocarbons as well as others may be used. Also, while satisfactory for use, fluorocarbons may be used as a propellant but for environmental and regulatory reasons their use is preferably avoided. In such an embodiment, the cleaning composition is dispensed by activating the release nozzle of said aerosol type container onto the soil and/or soil area, and in accordance with a manner as above-described a soil is treated and removed.

Whereas the present invention is intended to be produced and provided in the "ready-to-use" form described above, nothing in this specification shall be understood as to limit the use of the composition according to the invention with a further amount of water to form a cleaning solution therefrom. In such a proposed diluted cleaning solution, the greater the proportion of water added to form said cleaning dilution, the greater may be the reduction of the rate and/or efficacy of the thus formed cleaning solution in the cleaning of a hard surface, as well as a reduction in disinfectant efficacy. Accordingly, longer residence times upon the soil to effect their loosening and/or the usage of greater amounts may be necessitated. Such further diluted cleaning compositions may be easily prepared by diluting measured amounts of the compositions in further amounts of water by the consumer or other end user in certain weight ratios of composition:water, and optionally, agitating the same to ensure even distribution of the composition in the water. The aqueous compositions according to the invention may be used without further dilution, but may also be used with a further aqueous dilution, i.e., in composition:water concentrations of 1:0, to extremely dilute dilutions such as 1:10, 000. Desirably however, in order to ensure disinfection the compositions should be used "as is", that is to say without further dilution. However, aqueous dilutions, i.e., composition:water of concentrations of 1:1–3 are believed to exhibit good sanitizing efficacy, but which may require longer contact times in order to provide an adequate sanitizing effect. The actual dilution selected is in part determinable by the degree and amount of dirt and grime to be removed from a surface(s), the amount of mechanical force imparted to remove the same, as well as the observed efficacy of a particular dilution. Generally better results and faster removal is to be expected at lower relative dilutions of the composition and the water, with the best results expected when the inventive compositions are used without further dilution with water.

The following examples illustrate the superior properties of the formulations of the invention and particular preferred embodiments of the inventive compositions. The terms "parts by weight" or "percentage weight" are used interchangeably in the specification and in the following Examples wherein the weight percentages of each of the individual constituents are indicated in weight percent based on the total weight of the composition, unless indicated otherwise.

EXAMPLES

Exemplary formulations illustrating certain preferred embodiments of the inventive compositions and described in more detail in Table 1 below were formulated generally in accordance with the following protocol.

Into a suitably sized vessel, a measured amount of water was provided after which the constituents were added in the following sequence: surfactants, alcohol and glycol ethers, hydrogen peroxide, monoethanolamine, or acid and lastly the coloring and fragrance constituents (if included). All of the constituents were supplied at room temperature, and mixing of the constituents was achieved by the use of a mechanical stirrer with a small diameter propeller at the end of its rotating shaft. Mixing, which generally lasted from 5 minutes to 120 minutes was maintained until the particular exemplary formulation appeared to be homogeneous. The exemplary compositions were readily pourable, and retained well mixed characteristics (i.e., stable mixtures) upon standing for extended periods, even in excess of 120 days.

It is to be noted that the constituents might be added in any order, but it is preferred that water be the initial constituent provided to a mixing vessel or apparatus as it is the major constituent and addition of the further constituents thereto is convenient.

The exact compositions of the example formulations are listed on Table 1, below wherein are indicated the weight percentages of the individual constituents, based on a total composition weight of 100% weight.

TABLE 1

| Constituent: | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| quaternary amine surfactant[1] | 0.10 | 0.10 | 0.10 | 0.10 | 0.10 | 0.10 | 0.10 | 0.10 | 0.10 |
| quaternary amine surfactant[2] | | | | | | | | | |
| propylene glycol mono-n-butyl ether | 4.00 | 4.00 | — | 2.00 | — | 4.00 | — | — | 1.00 |
| dipropylene glycol mono-n-butyl ether | — | — | 3.00 | — | 3.00 | — | 3.00 | — | — |
| diethylene glycol mono-n-butyl ether | — | — | — | — | — | — | — | 6.00 | — |
| n-decanol | — | — | — | — | 0.035 | — | 0.040 | 0.10 | — |
| cocoamidopropyl betaine | — | 0.35 | — | — | — | — | — | — | — |
| lauryl dimethyl amine oxide | 0.81 | — | 0.44 | 0.35 | 0.44 | 0.35 | 0.90 | 0.90 | 0.10 |
| monoethanolamine | 0.50 | 0.50 | 0.50 | 0.50 | 0.50 | 0.50 | 0.50 | 0.50 | 0.10 |
| conventional additives | 0.15 | — | — | — | — | — | 0.20 | 0.20 | 0.02 |
| water | to 100 | to 100 | to 100 | to 100 | to 100 | to 100 | to 100 | to 100 | to 100 |

The source or identity of the particular constituents recited in Table 1 are disclosed in particular detail in Table 2 below.

TABLE 2

| Constituent: | |
|---|---|
| alkyl dimethyl benzyl ammonium chloride surfactant[1] | supplied in BTC-8358 ® from Stepan Co., Northfield IL. |
| alkyl benzyl quaternary ammonium surfactant[2] | supplied in BTC-65 ® from Stepan Co., Northfield IL. |
| propylene glycol mono-n-butyl ether | Dowanol ® PnB (Dow Chemical Co., Midland MI) |
| dipropylene glycol mono-n-butyl ether | Dowanol ® DPnB (Dow Chemical Co., Midland MI) |
| n-decanol | n-decanol |
| lauryl dimethyl amine oxide | supplied in Ammonyx ® LO |
| cocoamidopropyl betaine | supplied in Mackam ® DZ (McIntyre Group Ltd.) |

TABLE 2-continued

| Constituent: | |
|---|---|
| monoethanolamine | supplied by Dow Chemical Co. |
| conventional additives | fragrance oil, proprietary composition |
| water | deionized water |

The compositions of Table 1 were evaluated in accordance with one or more of the further tests elucidated below.

Evaluation of Antimicrobial Efficacy

Several of the exemplary formulations of Table 1 above were evaluated in order to evaluate their antimicrobial efficacy against *Staphylococcus aureus* (gram positive type pathogenic bacteria) (ATCC 6538), *Salmonella choleraesuis* (gram negative type pathogenic bacteria) (ATCC 10708), and *Pseudomonas aeruginosa* (ATCC 15442). The testing was performed in accordance with the protocols outlined in "Use-Dilution Method", Protocols 955.14, 955.15 and 964.02 described in Chapter 6 of "Official Methods of Analysis", 16th Edition, of the Association of Official Analytical Chemists; "Germicidal and Detergent Sanitizing Action of Disinfectants", 960.09 described in Chapter 6 of "Official Methods of Analysis", 15th Edition, of the Association of Official Analytical Chemists; or American Society for Testing and Materials (ASTM) E 1054-91 the contents of which are herein incorporated by reference. This test is also commonly referred to as the "AOAC Use-Dilution Test Method".

As is appreciated by the skilled practitioner in the art, the results of the AOAC Use-Dilution Test Method indicates the number of test substrates wherein the tested organism remains viable after contact for 10 minutes with a test disinfecting composition/total number of tested substrates (cylinders) evaluated in accordance with the AOAC Use-Dilution Test. Thus, a result of "0/60" indicates that of 60 test substrates bearing the test organism and contacted for 10 minutes in a test disinfecting composition, 0 test substrates had viable (live) test organisms at the conclusion of the test. Such a result is excellent, illustrating the excellent disinfecting efficacy of the tested composition.

Results of the antimicrobial testing are indicated on Table 3, below. The reported results indicate the number of test cylinders with live test organisms/number of test cylinders tested for each example formulation and organism tested.

TABLE 3

ANTIMICROBIAL EFFICACY

| Example Formulation | Staphylococcus aureus | Salmonella choleraesuis | Pseudomonas aeruginosa |
|---|---|---|---|
| Ex. 1 | 0/10 | 0/10 | 0/10 |
| Ex. 2 | 0/30 | 0/20 | 0/60 |
| Ex. 3 | 0/20 | 0/20 | 0/20 |
| Ex. 6 | 0/30 | 0/20 | 0/60 |

As may be seen from the results indicated above, the compositions according to the invention provide excellent disinfection of hard surfaces.

Evaluation of Shelf Stability

Compositions according to the invention and described on Table 1 above were placed in sealed containers, and subjected to an accelerated aging test wherein the compositions were maintained at 120° F. for a period of 4 weeks. Subsequent to this treatment, the compositions were observed to be a single phase mixture; bulk phase separation was not observed to occur.

Evaluation of Cleaning Efficacy

Various formulations amongst those listed above were evaluated for their cleaning efficacy by visual inspection. These testing was a simple visual screening performed was generally in accordance with ASTM Test 4488 (Annex A2) "Greasy Soil/Painted Masonite Wallboard Test Method" using a BYK-Gardner Abrasion Tester. Evaluation of the cleaning efficacy was by visual assessment by a panel of persons who evaluated the tested compositions and substrates. Equal amount of each tested formulation, which compared Ex. 7 and the following commercially available formulations. All formulations were used "as is" without any further dilution. The results of the test are provided in Table 4, wherein the percentages indicate the averaged value (at a 95% confidence level) of the 'percentage soil removed' as provided by the evaluation panel.

TABLE 4

| Formulation | % soil removed (averaged) |
|---|---|
| Example 7 | 86.51% |
| Formula 409 ® (Clorox Co.) | 84.64% |
| Formula 409 ® 'Now Kills Bacteria' (Clorox Co.) | 83.00% |
| DOW Antibacterial Kitchen Cleaner (Dow Brands Inc.) | 84.20% |

As the results of Table 4 indicate, the formulation according to the invention was superior to other commercially available products.

Evaluation of Evaporation and Drying Characteristics

In the test were used as substrates a black glazed ceramic tile, and a polished stainless steel tile. Onto the surface of the each horizontally positioned tile was deposited a drop of a composition according to Table 1, and using a clean lint free paper wipe (Kimwipe®, available from Kimberly-Clark Corp.) crumpled into a ball the deposited drop was spread into a roughly circular pattern to form a generally uniform thin film of the composition onto the surface of the test substrate. This film was approximately 1 inch in diameter. The drying behavior of the thus deposited composition was observed, and in each instance it was noted that drying was generally uniform with evaporation beginning at the margins of the circular film and generally uniformly proceeding towards the center of the film. During drying, no discrete rivulets or droplets were formed, leaving dry surface. Typically total drying took no more than 1–1½ minutes, with virtually no visible surface residue on the surface of the black glazed ceramic tile, and with only a very faint dark color cast on the polished stainless steel tile surface which had been wetted by the composition. This color cast was easily removed by wiping with a clean and dry lint free paper wipe.

While described in terms of the presently preferred embodiments, it is to be understood that the present disclosure is to be interpreted as by way of illustration, and not by way of limitation, and that various modifications and alterations apparent to one skilled in the art may be made without departing from the scope and spirit of the present invention.

I claim:

1. An aqueous hard surface cleaning and broad spectrum disinfecting composition comprising:

0.05 –0.3% wt. of a quaternary ammonium surfactant compound having germicidal properties;

0.001–6.15% wt. of an organic solvent system which consists of dipropylene glycol n-butyl ether and a $C_6$–$C_{18}$ linear primary alcohol;

0.1–3.0% wt. of one or more amine oxide compounds;
0.1–0.5% wt. of one or more alkanolamines;
0–0.5% wt. of one or more optional constituents;
to 100% water.

2. An aqueous hard surface cleaning and broad spectrum disinfecting composition comprising:
0.05–0.3% wt. of a quaternary ammonium surfactant compound having germicidal properties;
0.001–6% wt. of an organic solvent system which consists of propylene glycol mono-n-butyl ether;
0.1–3.0% wt. of one or more amine oxide compounds;
0.1–0.5% wt. of one or more alkanolamines;
0–0.5% wt. of one or more optional constituents;
to 100% water.

3. The low residue hard surface cleaning and disinfecting composition according to claim 1 wherein the one or more alkanolamines are mono-, di- or tri-alkanolamine.

4. The low residue hard surface cleaning and disinfecting composition according to claim 1 wherein the quaternary ammonium germicide is in accordance with the following general structural formula:

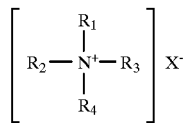

where:
at least one of $R_1$, $R_2$, $R_3$ and $R_4$ is a alkyl, aryl or alkylaryl substituent of from 6 to 26 carbon atoms, which may include one or more amide, ether or ester linkages;
remaining $R_1$, $R_2$, $R_3$ and $R_4$ are straight-chained or branched, hydrocarbons usually containing not more than 12 carbon atoms, which may include one or more amide, ether or ester linkages;
and, X is a salt-forming anion.

5. The low residue hard surface cleaning and disinfecting composition according to claim 4 wherein the quaternary ammonium germicide is in accordance with the following general structural formula:

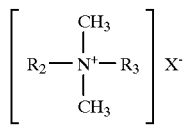

where:
$R_2$, $R_3$ may be $C_8$–$C_{12}$alkyl, or when $R_2$ is $C_{12-16}$alkyl, $C_{8-18}$alkylethoxy,
$C_{8-18}$alkylphenolethoxy, $R_3$ is benzyl;
X is a halide.

6. A composition according to claim 1 further characterized in that the composition forms a substantially uniform film during evaporative drying subsequent to application on a hard surface.

7. A composition according to claim 1 further characterized in that the composition is phase stable when subjected to an elevated temperature of 120° F. for a period of at least 4 weeks.

8. A process for the cleaning and disinfecting of a hard surface in need of such treatment which comprises the step of:
applying an effective amount of the composition according to claim 1.

9. The low residue hard surface cleaning and disinfecting composition according to claim 1 which further comprises one or more nonionic surfactant compounds.

10. The low residue hard surface cleaning and disinfecting composition according to claim 2 wherein the one or more alkanolamines are mono-, di- or tri-alkanolamine.

11. The low residue hard surface cleaning and disinfecting composition according to claim 2 wherein the quaternary ammonium germicide is in accordance with the following general structural formula:

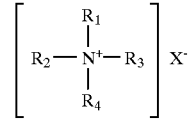

where:
at least one of $R_1$, $R_2$, $R_3$ and $R_4$ is a alkyl, aryl or alkylaryl substituent of from 6 to 26 carbon atoms, which may include one or more amide, ether or ester linkages;
remaining $R_1$, $R_2$, $R_3$ and $R_4$ are straight-chained or branched, hydrocarbons usually containing not more than 12 carbon atoms, which may include one or more amide, ether or ester linkages;
and, X is a salt-forming anion.

12. The low residue hard surface cleaning and disinfecting composition according to claim 11 wherein the quaternary ammonium germicide is in accordance with the following general structural formula:

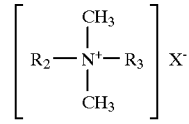

where:
$R_2$, $R_3$ may be $C_8$–$C_{12}$alkyl, or when $R_2$ is $C_{12-16}$alkyl, $C_{8-18}$alkylethoxy, $C_{8-18}$alkylphenolethoxy, $R_3$ is benzyl;
X is a halide.

13. A composition according to claim 2 further characterized in that the composition forms a substantially uniform film during evaporative drying subsequent to application on a hard surface.

14. A composition according to claim 2 further characterized in that the composition is phase stable when subjected to an elevated temperature of 120° F. for a period of at least 4 weeks.

15. A composition according to claim 2 which comprises:
1.0–4.5% wt of an organic solvent system which consists of propylene glycol mono-n-butyl ether.

16. The low residue hard surface cleaning and disinfecting composition according to claim 1 which further comprises one or more nonionic surfactant compounds.

17. A process for the cleaning and disinfecting of a hard surface in need of such treatment which comprises the step of:
applying an effective amount of the composition according to claim 2.

* * * * *

UNITED STATES PATENT AND TRADEMARK OFFICE
CERTIFICATE OF CORRECTION

PATENT NO. : 5,929,016
DATED : 27 July 1999
INVENTOR(S) : Kenneth A. HARRISON

It is certified that error appears in the above-identified patent and that said Letters Patent is hereby corrected as shown below:

At column 16, line 65, delete "6.15%" and insert --6%--.

Signed and Sealed this

Twenty-first Day of December, 1999

*Attest:*

Q. TODD DICKINSON

*Attesting Officer*     *Acting Commissioner of Patents and Trademarks*